United States Patent [19]
Goodin et al.

[11] Patent Number: 5,670,495
[45] Date of Patent: Sep. 23, 1997

[54] METHOD OF PRETREATING AN ANIMAL WITH A CORTICOSTEROID PRIOR TO INFUSION OF A PERFLUOROCHEMICAL EMULSION

[75] Inventors: Thomas H. Goodin, Manchester; Robert J. Kaufman, University City, both of Mo.

[73] Assignee: HemaGen/PFC, St. Louis, Mo.

[21] Appl. No.: 637,580

[22] Filed: Apr. 25, 1996

Related U.S. Application Data

[63] Continuation of Ser. No. 331,326, Oct. 28, 1994, abandoned.

[51] Int. Cl.$^6$ .................................................. A61K 31/56
[52] U.S. Cl. ........................... 514/178; 514/177; 514/759
[58] Field of Search ................................. 514/178, 177, 514/759

[56] References Cited

PUBLICATIONS

*Artif. Cells Blood Substitutes Immobilization Biotechnol.,* Perfluorocarbons as blood substitutes: the early years, Experience with Fluosol DA–20% in the 1980s, vol. 22, No. 4, Sep. 1994, pp. 955–963, Riess, J.G.

*Rev. Fr. Transfus. Hemobiol.,* Les emulsions de fluorocarbures comme transporteurs d–oxyene injectables. Progres recents et perspectives, vol. 35, No. 6, pp. 391–406, 1992, Riess, J.G.

*Blood,* Activation of plasma complement by perfluorocarbon aritificial blood: probable mechanism of adverse pulmonary reactions in treated patients and rationale for corticosteroid prophylaxis, vol. 59, No. 6, pp. 1299–1304, 1982, Vercellotti et al.

*FASEB J.,* Prophylaxis with corticosteroids and cyclooxygenase inhibitors: effect on the delayed febrile response after intravenous infusion of perfluorochemical emulsions in conscious swine, vol. 6, No. 4, 1992, p. A1055, Abstract No. 689, Flaim et al.

*Scanning Electron. Microscop.,* Endothelial response to perfluorochemical perfusion. vol. 1984/1, pp. 315–316, 1984, McCoy, L.E. et al.

S. F. Flaim, et al., "Characterization and Mechanism of Side Effects of Imagent BP (Highly Concentrated Fluorocarbon Emulsion) In Swine", vol. 26, Investigative Radiology, Nov. Supplement 1991, S122–S124.

Hainsey, B. M. et al. "Clinical Parameters of the Normal Baboons (Papio species) and Chimpanzees (*Pan troglodytes*)", vol. 43, No. 3, Laboratory Animal Science, Jun., 1993.

Hollace M. Feingold, et al., "Coagulation Assays and Platelet Aggregation Patterns in Human, Baboon, and Canine Blood", vol. 47, No. 10, American Journal of Veterinary Research, Oct., 1986.

*Primary Examiner*—Marianne M. Cintins
*Assistant Examiner*—Dwayne C. Jones
*Attorney, Agent, or Firm*—Wood, Herron & Evans, L.L.P.

[57] ABSTRACT

This invention is directed to a method of attenuating or preventing the adverse side-effects of a perfluorochemical (PFC) emulsion on the hemostatic system and serum chemistry of an animal. The method includes intravenously administering a corticosteroid to an animal prior to intravenous administration of a PFC emulsion, in an amount sufficient to improve the adverse effects of the PFC upon the hemostatic system and serum triglyceride/enzyme levels of the animal. After administration of the corticosteroid, the PFC emulsion is administered intravenously. Preferably, the corticosteroid is dexamethasone, and the PFC is perfluorodichlorooctane.

10 Claims, No Drawings

METHOD OF PRETREATING AN ANIMAL WITH A CORTICOSTEROID PRIOR TO INFUSION OF A PERFLUOROCHEMICAL EMULSION

This application is a continuation, of application Ser. No. 08/331,326, filed Oct. 28, 1994 now abandoned.

BACKGROUND OF THE INVENTION

1. Field of the Invention

This invention is directed to the use of corticosteroids, and more particularly, to the use of corticosteroids for reducing or attenuating the adverse effects of a perfluorochemical emulsion on the hemostatic system and serum chemistry parameters of an animal.

2. Description of the Related Art

Perfluorochemical (PFC) emulsions are being developed for many different uses. Because PFCs have a high intrinsic solubility for gases, including $O_2$ and $CO_2$, they are especially useful as $O_2/CO_2$ transport agents, artificial bloods, and red blood cell substitutes. PFC emulsions also are being developed as contrast agents for biological imaging. However, one of the drawbacks in using PFC emulsions in animals is that these emulsions produce certain undesirable side effects.

Side effects from the intravenous infusion of a PFC emulsion have been reported in both human and animal studies. Two groups of side effects have been observed in human volunteers receiving a perfluorooctylbromide (PFOB) emulsion. PFOB, also known as Perflubron, is a PFC under development as a component of a blood-pool imaging agent known as Imagent BP. Imagent BP is a phospholipid emulsion containing ninety (90%) percent w/v Perflubron and having a mass median particle size of approximately 0.2μ. The first group of side effects occurs within the first 2 hours after injection of the PFC emulsion. These acute effects are characterized primarily by skin flushing and backache. The second group of side effects occurs later than 2 hours post-injection and lasts generally for about a day. These delayed effects, described as a "flu-like syndrome", include fever, dizziness, and occasional nausea. S. F. Flaim, et al., "Characterization and Mechanism of Side Effects of Imagent BP (Highly Concentrated Fluorocarbon Emulsion) In Swine", Vol. 26, *Investigative Radiology*, November Supplement 1991, S122–S124.

PFC emulsions also induce adverse side effects in swine. As with the human volunteers, intravenous administration of a PFOB emulsion produced both an acute and a delayed response in swine. The acute response included a rise in mean pulmonary artery pressure (mPAP) and severe skin flushing, both of which resolved completely by 2 hours post-injection. The delayed side effect was a febrile response characterized by a 1°–2° C. increase in body temperature which peaked at 4 hours post-injection and resolved over the next 2 to 24 hours. The early rise in mPAP is believed to be related to the activation of pulmonary intravascular macrophages, while the skin flushing is attributed to the substantial release of Prostaglandins upon macrophage activation. S. F. Flaim, et al., "Characterization and Mechanism of Side Effects of Imagent BP (Highly Concentrated Fluorocarbon Emulsion) In Swine", Vol. 26, *Investigative Radiology*, November Supplement 1991, S122–S124.

Further research with swine has shown that these particular clinical side effects may be effectively prophylaxed with dexamethasone, ibuprofen, or indomethacin. For example, the acute, transient rise in mPAP and skin flushing both were blocked successfully by prophylaxis with any one of these three compositions. In addition, the delayed febrile response also was blocked successfully by prophylaxis with dexamethasone, ibuprofen, or indomethacin. Id.

Despite the advances made by these animal and human studies, they do not identify other problems or side effects which might be associated with intravenous infusion of PFC emulsions. Given the increase in clinical use of such emulsions, it would be desirable to identify other potential side effects. Furthermore, once those side effects have been identified, it would be highly beneficial to identify ways in which those side effects might be alleviated or even prevented.

SUMMARY OF THE INVENTION

This invention is directed to a method of improving the adverse effects of a perfluorochemical emulsion on the hemostatic system and serum chemistry of an animal. The method includes intravenously administering a corticosteroid to an animal prior to intravenous administration of a perfluorochemical emulsion. The corticosteroid is administered in an amount sufficient to improve the adverse effects of the perfluorochemical upon the hemostatic system and serum triglyceride/enzyme levels of the animal. After administration of the corticosteroid, the perfluorocarbon emulsion is administered intravenously.

Preferably, the corticosteroid is administered at a dose of from about 0.2 mg/kg of body weight to about 6 mg/kg of body weight, and more preferably, at a dose of about 1 mg/kg. The perfluorochemical used in the perfluorochemical emulsion preferably is administered at a dose of from about 0.5 to about 10 ml/kg of body weight.

With respect to the hemostatic system, the method may be conducted for reducing perfluorochemical-induced adverse side effects upon prothrombin time and activated partial thromboplastin time, and for inhibiting perfluorochemical-induced thrombocytopenia. With respect to serum chemistry, the method may be conducted for reducing perfluorocarbon-induced adverse side effects upon aspartate amino transferase enzyme activity, lactate dehydrogenase enzyme activity and bilirubin.

The corticosteroid preferably is dexamethasone, while the perfluorochemical preferably is selected from the group consisting of: perfluorodichlorooctane, perfluorodecalin, perfluoromethyldecalin, perfluorodimethyldecalin, perfluorodimethyladamantane, perfluorooctylbromide, perfluoro-4-methyl-octahydroquinolidizine, perfluoro-N-methyldecahydroquinoline, F-methyl-1-oxa-decalin, perfluorobicyclo(5.3.0)decane, perfluorooctahydroquinolidizine, perfluoro-5,6-dihydro-5-decene, and perfluoro-4,5-dihydro-4-octene, chlorinated perfluorocarbons, and mixtures thereof. Most preferably, the perfluorochemical used in the method is perfluorodichlorooctane.

The perfluorochemical emulsion preferably contains the perfluorochemical in an amount of from about 15 v/v % to about 70 v/v %, and more preferably, in an amount of about 40 v/v %.

With respect to the timing of the method steps, administration of the perfluorochemical emulsion preferably is begun within several hours after administering the corticosteroid, and can also be administered immediately following administration of the corticosteroid.

This invention offers several benefits to animals being treated with PFC emulsions. For example, corticosteroid pretreatment attenuates or prevents adverse PFC-induced side effects on the coagulation system. Pretreatment virtually eliminates the PFC-induced adverse effects on prothrombin time and activated partial thromboplastin time, and significantly inhibits PFC-induced thrombocytopenia.

Corticosteroid pretreatment also attenuates or eliminates adverse PFC-induced side effects on several serum chemistry parameters. For example, pretreatment inhibits PFC-induced increases in serum triglycerides and bilirubin, as well as in aspartate amino transferase enzyme activity and lactate dehydrogenase enzyme activity.

DETAILED DESCRIPTION OF THE INVENTION

This invention is directed to a method of improving the adverse effects of a perfluorochemical emulsion on the hemostatic system and serum chemistry of an animal. The method includes intravenously administering a corticosteroid to an animal prior to intravenous administration of a perfluorochemical emulsion. The corticosteroid is administered in an amount sufficient to improve the adverse effects of the perfluorochemical upon the hemostatic system and serum triglyceride/enzyme levels of the animal. After administration of the corticosteroid, the perfluorocarbon emulsion is administered intravenously.

Preferably, the corticosteroid is administered at a dose of from about 0.2 mg/kg of body weight to about 6 mg/kg of body weight. At low doses of about 0.1 mg/kg, pretreatment with dexamethasone has little impact on PFC-induced side effects; while doses above about 6.0 mg/kg present safety issues in that such doses may result in undesired changes in the hypothalamic-pituitary-adrenal axis physiology. More preferably, the corticosteroid is administered at a dose of about 1 mg/kg. The perfluorochemical used in the perfluorochemical emulsion preferably is administered at a dose of from about 0.5 to about 10 ml/kg of body weight.

With respect to the hemostatic system, the method may be conducted for reducing perfluorochemical-induced adverse side effects upon prothrombin time and activated partial thromboplastin time, and for inhibiting perfluorochemical-induced thrombocytopenia. With respect to serum chemistry, the method may be conducted for reducing perfluorocarbon-induced adverse side effects upon aspartate amino transferase enzyme activity, lactate dehydrogenase enzyme activity and bilirubin.

The corticosteroid preferably is dexamethasone. The perfluorochemical preferably is selected from the group consisting of perfluorodichlorooctane, perfluorodecalin, perfluoromethyldecalin, perfluorodimethyldecalin, perfluorodimethyladamantane, perfluorooctylbromide, perfluoro-4-methyl-octahydroquinolidizine, perfluoro-N-methyl-decahydroquinoline, F-methyl-1-oxa-decalin, perfluoro-bicyclo(5.3.0)decane, perfluorooctahydroquinolidizine, perfluoro-5,6-dihydro-5-decene, and perfluoro-4,5-dihydro-4-octene, chlorinated perfluorocarbons, and mixtures thereof. Most preferably, the perfluorochemical used in the method is perfluorodichlorooctane.

The perfluorochemical emulsion preferably contains the perfluorochemical in an amount of from about 15 v/v % to about 70 v/v %, and more preferably, in an amount of about 40 v/v %.

With respect to the timing of the method steps, administration of the perfluorochemical emulsion preferably is begun within several hours after administering the corticosteroid, and can also be administered immediately following administration of the corticosteroid.

EXAMPLE

Study Design and Protocol

A study was conducted to assess the responses associated with an acute intravenous exposure of a 40 v/v % perfluorodichlorooctane (PFDCO) emulsion in male adult baboons (*Papio cynocephalus*) with and without treatment with 1 mg/kg of dexamethasone. Dose levels of the 40 v/v % PFDCO emulsion were selected to impart minimal, reversible side effects in the baboon that would be efficacious with respect to intravascular gas transport. The dexamethasone pretreatment regimen was administered intravenously at a dose level intended to elicit anti-inflammatory effects. The 40 v/v % PFDCO emulsion included a PFDCO stem emulsion, as well as a 23.4% saline annex solution. The specific composition of the stem emulsion, saline annex and final formulation is shown in Table 1.

TABLE 1

Formulation of the 40 v/v % PFDCO Emulsion

| Component | PFDCO Stem Emulsion | 23.4% Saline Annex | Final Formulation for IV Administration |
|---|---|---|---|
| PFDCO (v/v %) | 40 | — | 39 |
| Lecithin (w/v %) | 2 | — | 1.95 |
| Safflower Oil (w/v %) | 2 | — | 1.95 |
| Na$_2$CO$_3$ (w/v %) | 0.015 | — | — |
| NaCl (w/v %) | — | 23.4 | 0.466 |
| Water for Injection | q.s | q.s | q.s |

Twelve adult male baboons (*Papio cynocephalus*) were selected after being given complete health examinations by veterinary personnel and approved for the study. The animals ranged in age from 8–20 years, were either feral or colony born, and were clinically in excellent health.

The twelve animals were divided into four treatment groups with three animals in each group. The group I and II animals each received 1.0 ml/kg PFDCO (2.5 ml/kg stem emulsion annexed with 23.4% sodium chloride), with the Group II animals also receiving 1 mg/kg dexamethasone intravenously immediately prior to infusion of PFDCO. The Group III and IV animals each received 2.0 ml/kg PFDCO (5.0 ml/kg stem emulsion mixed with 23.4% sodium chloride), while the Group IV animals also received 1 mg/kg dexamethasone intravenously immediately prior to infusion.

The baboons were sedated for dexamethasone and PFDCO infusion with ketamine HCl (IM) supplemented with valium, and additional doses of ketamine HCl were administered when required to maintain sedation. Following sedation and pretreatment blood collection, a 16–20 gauge indwelling angiocatheter was placed and secured into a saphenous vein for infusion of the respective emulsions. The doses of the 40 v/v % PFDCO emulsion were administered at a rate of approximately 4–6 ml per minute.

Blood samples were drawn and analyzed over a thirty (30) day period following administration of the PFDCO emulsion. The baboons were sedated for all blood sampling procedures with ketamine HCl (IM) supplemented with valium, and additional doses of ketamine HCl were administered when required to maintain sedation. Indirect systemic blood pressure was measured using a non-invasive blood pressure unit, and body temperature was monitored using a rectal thermometer. In addition, respiratory rate was measured directly by monitoring the inspiratory excursions of the thoracic or abdominal wall, while heart rate was determined by palpation of a peripheral pulse or chest auscultation. Blood samples were collected percutaneously via a peripheral vein.

Data Analysis Methodology

For parameters having multiple baseline and/or pre-infusion measurements, an average baseline value for each animal was calculated. The change in response from the average baseline was statistically evaluated, and between-group comparisons at each dose level of PFC with and without dexamethasone pretreatment were performed at each sample time. A one-factor analysis of variance (ANOVA) was used to test for significance within and between groups over time. The levels of significance were defined as $P<0.05$ and $P<0.01$.

The results presented below were compared to normal values for the adult male baboon as listed in Brenda M. Hainsey, et al., "Clinical Parameters of the Normal Baboons (Papio species) and Chimpanzees (Pan troglodytes)", Vol. 43, No. 3, Laboratory Animal Science, June, 1993. For analysis of Factor VIII, the results were compared to the normal range for baboons as reported in Hollace M. Feingold, et al., "Coagulation Assays and Platelet Aggregation Patterns in Human, Baboon, and Canine Blood", Vol. 47, No. 10, American Journal of Veterinary Research, October, 1986.

Impact of Dexamethasone Pretreatment on the Hemostatic System

Prothrombin time (PT) is shown for the four treatment groups over the length of the study in Table 2. In the low dose PFC animals, there was evidence of a rise in the PT at six hours post-infusion, which remained elevated one day after infusion. However, in the low dose animals pretreated with dexamethasone, there were no significant changes in the PT over the course of the study. In the high dose baboons, the PT was significantly elevated at 4 hours, 6 hours, and 1 day post-infusion when compared to the baseline and the high dose animals pretreated with dexamethasone. At 2 days following dosing, the PT of the high dose animals remained significantly prolonged when compared to the baseline. For the pretreated high dose animals, the only significant change in the PT from baseline occurred at thirty (30) days post-infusion; however, this elevation was not considered to be biologically significant.

The activated partial thromboplastin time (aPTT) results are presented in Table 3. On day 1 post-infusion, the low dose animals showed a significantly higher aPTT when compared with the pretreated low dose animals. In the high dose baboons, the aPTT was significantly elevated at 4 hours, 6 hours, and 1 day post-infusion when compared to the baseline and the pretreated high dose animals. On day 7, the aPTT of the high dose animals decreased significantly from baseline, although this was not considered to be biologically significant. Meanwhile, in the high dose animals pretreated with dexamethasone, there was no significant change in the aPTT from baseline, and the clotting times were all within normal range for the baboon.

The Factor VIII (FVIII) results are summarized in Table 4. FVIII levels of the low dose and pretreated low dose groups showed some scattered significant differences from baseline and between treatments, however, all of the values were within the normal range for baboons. The FVIII levels of the high dose animals exceeded the upper limit of the normal range on days 2, 4, 7, and 14 post-dosing. Values for the pretreated high dose animals also exceeded the upper limit of the normal range, but only at six hours, 1 day and 2 days post-dosing, coming back into the normal range much sooner than the values for the untreated animals.

The plasma fibrinogen values for the various treatment groups are shown in Table 5. In the low dose baboons, the fibrinogen concentration exceeded the upper limit of the normal range (214 mg/dl) on days 1 and 2, and was significantly different from baseline on day 2. The fibrinogen concentrations in the pretreated low dose baboons also exceeded the upper limit of the normal range on days 1 and 2, however, these changes were not considered to be biologically significant. The fibrinogen concentration of the high dose group decreased significantly with respect to baseline at six hours post-infusion, and this concentration was below the lower limit of normal (118 mg/dl) for baboons. Meanwhile, fibrinogen levels in the pretreated high dose group increased significantly from baseline on days 1 and 2 and exceeded the upper limit of normal on days 1, 2, and 4.

Intravenous administration of PFDCO also induced thrombocytopenia in the untreated study groups. The platelet count data for the four study groups is shown in Table 6. The normal range for a baboon platelet count is 164,000–394,000/mm$^3$, with values below this range indicative of thrombocytopenia. In comparison to the low end of the normal range, the low dose baboons were moderately to mildly thrombocytopenic on days 4 and 7 post-infusion. Meanwhile, the pretreated low dose animals were not considered to be thrombocytopenic since the platelet count values for these animals were within the normal range during the entire study. Meanwhile, both high dosed study groups exhibited signs of thrombocytopenia. However, the untreated high dose animals were thrombocytopenic between days 2 and 14, whereas the thrombocytopenia in the treated high dose group was not visible until day 4.

Impact of Dexamethasone Pretreatment on Serum chemical Parameters

Clinical chemistry parameters were analyzed only for the two high dose study groups.

Serum triglyceride (TG), total bilirubin, and direct bilirubin values are shown in Tables 7 and 8. With respect to serum triglycerides, elevations in the high dose animals exceeded the upper limit (94 mg/dl) of the normal range for baboons on days 1, 2, and 4, whereas increases in the dexamethasone pretreated group were well within the normal range for the baboon. The TG increases were probably related to the infusion of exogenous triglycerides contained in the corticosteroid and/or PFC emulsion and the number of chemical sedation procedures required for blood sampling and monitoring of vital signs in the first 4 days post-infusion.

The total bilirubin values exceeded or were at the upper limit (0.40 mg/dl) of normal for baboons at 4 hours, 6 hours, and 1 day in the high dose animals, and were at this upper limit at 4 hours and 6 hours in the pretreated animal group. These rises probably were due to altered hemoglobin metabolism secondary to phagocytosis of the emulsion particles by the hepatic reticuloendothelial (Kupffer) cells. With respect to direct bilirubin, the high dose group exceeded the normal range for baboons (0.20mg/dl) at 6 hours and 1 day post-infusion, whereas all of the values in the pretreatment group were within the normal range.

Aspartate amino transferase (AST) enzyme activity values are shown in Table 9. The AST enzyme activity exceeded the upper limit (62 U/L) of the normal range for baboons in both the high dose and pretreated high dose study groups at 4 hours, 6 hours, 1 day, 2 days and 4 days post-infusion. However, the AST values for the high dose group were significantly greater than the values of the pretreatment high dose group at 6 hours, 1 day and 2 days post-infusion.

The lactate dehydrogenase (LDH) serum enzyme activity values also are shown in Table 9. In the high dose animals, there is a significant elevation of LDH during several measurement times post-infusion, and all of the LDH values between 4 hours and 4 days were above the upper limit (438 U/L) of the normal range for baboons. In the pretreated high dose group, LDH values exceeded the upper limit of the normal range only on days 1 and 2. Furthermore, in this group, there were no significant changes in the LDH level from baseline over the course of the entire study.

This invention offers several benefits to animals being treated with PFC emulsions. For example, corticosteroid pretreatment attenuates or prevents adverse PFC-induced side effects on the coagulation system. Pretreatment virtually eliminates the PFC-induced adverse effects on prothrombin time and activated partial thromboplastin time, and significantly inhibits PFC-induced thrombocytopenia.

Corticosteroid pretreatment also attenuates or eliminates adverse PFC-induced side effects on several serum chemistry parameters. For example, pretreatment inhibits PFC-induced increases in serum triglycerides and bilirubin, as well as in aspartate amino transferase enzyme activity and lactate dehydrogenase enzyme activity.

TABLE 2

| | | Prothrombin Time (seconds) | | | |
|---|---|---|---|---|---|
| | | 1 ml/kg PFC | 1 ml/kg PFC Dexam | 2 ml/kg PFC | 2 ml/kg PFC Dexam |
| Baseline | Mean | 12.8 | 12.4 | 12.8 | 13.2 |
| | Std | 0.0 | 0.5 | 0.3 | 0.5 |
| | n | 3 | 3 | 3 | 3 |
| 4 Hour | Mean | 12.5 | 12.3 | 14.3†@ | 12.8 |
| | Std | 0.0 | 0.3 | 0.6 | 0.6 |
| | n | 3 | 3 | 3 | 3 |
| 6 Hour | Mean | 14.2 | 13.7 | 18.0†@ | 13.7 |
| | Std | 1.2 | 1.5 | 0.9 | 0.8 |
| | n | 3 | 3 | 3 | 3 |
| 1 Day | Mean | 14.4* | 13.5 | 16.0†@ | 14.0 |
| | Std | 1.7 | 1.3 | 0.5 | 0.5 |
| | n | 3 | 3 | 3 | 3 |
| 2 Day | Mean | 13.2 | 13.2 | 14.2† | 14.0 |
| | Std | 0.8 | 1.0 | 0.8 | 0.5 |
| | n | 3 | 3 | 3 | 3 |
| 4 Days | Mean | 12.5 | 12.7 | 12.8 | 13.8 |
| | Std | 0.5 | 0.8 | 0.3 | 0.3 |
| | n | 3 | 3 | 3 | 3 |
| 7 Days | Mean | 13.0 | 12.5 | 12.3 | 13.0 |
| | Std | 0.5 | 0.5 | 0.3 | 0.5 |
| | n | 3 | 3 | 3 | 3 |
| 14 Days | Mean | 13.0 | 12.7 | 13.0 | 13.3 |
| | Std | 0.5 | 0.6 | 0.5 | 0.6 |
| | n | 3 | 3 | 3 | 3 |
| 30 Days | Mean | 13.0 | 12.8 | 13.7 | 14.2* |
| | Std | 0.5 | 0.3 | 0.3 | 0.8 |
| | n | 3 | 3 | 3 | 3 |

*Denotes a significant difference from baseline (p ≤ 0.05)
_Denotes a significant difference within a PFC dose group with and without pretreatment (p ≤ 0.05)
†Denotes a significant difference from baseline (p ≤ 0.01)
@Denotes a significant difference within a PFC dose group with and without pretreatment (p ≤ 0.01)

TABLE 3

| | | Activated Partial Thromboplastin Time (aPTT) (seconds) | | | |
|---|---|---|---|---|---|
| | | 1 ml/kg PFC | 1 ml/kg PFC Dexam | 2 ml/kg PFC | 2 ml/kg PFC Dexam |
| Baseline | Mean | 31.4 | 29.3 | 32.9 | 33.1 |
| | Std | 0.8 | 1.6 | 4.1 | 1.6 |
| | n | 3 | 3 | 3 | 3 |
| 4 Hour | Mean | 29.3 | 28.3 | 39.5@ | 29.2 |
| | Std | 2.5 | 1.9 | 6.1 | 1.8 |
| | n | 3 | 3 | 3 | 3 |
| 6 Hour | Mean | 33.3 | 31.7 | 44.5†@ | 31.5 |
| | Std | 4.1 | 2.0 | 9.0 | 1.3 |
| | n | 3 | 3 | 3 | 3 |
| 1 Day | Mean | 36.2 | 29.7 | 43.7†@ | 32.2 |
| | Std | 7.7 | 3.4 | 6.8 | 2.0 |
| | n | 3 | 3 | 3 | 3 |
| 2 Day | Mean | 30.5 | 28.3 | 35.2† | 29.5 |
| | Std | 3.0 | 3.0 | 5.0 | 1.3 |
| | n | 3 | 3 | 3 | 3 |
| 4 Days | Mean | 26.7 | 29.3 | 27.2 | 32.0 |
| | Std | 1.3 | 2.6 | 2.6 | 2.2 |
| | n | 3 | 3 | 3 | 3 |
| 7 Days | Mean | 28.3 | 28.7 | 26.0* | 31.8 |
| | Std | 2.0 | 2.3 | 2.6 | 3.5 |
| | n | 3 | 3 | 3 | 3 |
| 14 Days | Mean | 30.5 | 31.7 | 29.8 | 31.3 |
| | Std | 1.8 | 2.5 | 3.3 | 3.5 |
| | n | 3 | 3 | 3 | 3 |
| 30 Days | Mean | 31.7 | 30.7 | 31.3 | 33.5 |
| | Std | 2.9 | 2.0 | 3.3 | 1.7 |
| | n | 3 | 3 | 3 | 3 |

*Denotes a significant difference from baseline (p ≤ 0.05)
_Denotes a significant difference within a PFC dose group with and without pretreatment (p ≤ 0.05)
†Denotes a significant difference from baseline (p ≤ 0.01)
@Denotes a significant difference within a PFC dose group with and without pretreatment (p ≤ 0.01)

TABLE 4

| | | Factor VIII (FVIII) (%) | | | |
|---|---|---|---|---|---|
| | | 1 ml/kg PFC | 1 ml/kg PFC Dexam | 2 ml/kg PFC | 2 ml/kg PFC Dexam |
| Baseline | Mean | 64.5 | 77.0 | 63.2 | 61.7 |
| | Std | 10.7 | 4.8 | 5.8 | 18.9 |
| | n | 3 | 3 | 3 | 3 |
| 4 Hour | Mean | 77.3 | 89.3 | 74.0 | 87.0 |
| | Std | 8.6 | 20.5 | 16.6 | 43.6 |
| | n | 3 | 3 | 3 | 3 |
| 6 Hour | Mean | 89.3* | 65.7 | 89.0 | 105.0* |
| | Std | 2.5 | 21.2 | 38.0 | 33.0 |
| | n | 3 | 3 | 3 | 3 |
| 1 Day | Mean | 58.3 | 92.0 | 61.0 | 100.7 |
| | Std | 16.5 | 25.0 | 8.5 | 38.6 |
| | n | 3 | 3 | 3 | 3 |
| 2 Day | Mean | 76.3 | 87.0 | 98.7 | 116.7* |
| | Std | 13.4 | 15.0 | 8.7 | 23.4 |
| | n | 3 | 3 | 3 | 3 |
| 4 Days | Mean | 78.7 | 70.7 | 105.0* | 77.0 |
| | Std | 11.6 | 3.2 | 7.5 | 22.1 |
| | n | 3 | 3 | 3 | 3 |
| 7 Days | Mean | 67.0 | 93.3 | 113.3* | 83.0 |
| | Std | 8.7 | 15.5 | 7.8 | 29.5 |
| | n | 3 | 3 | 3 | 3 |
| 14 Days | Mean | 60.7 | 54.3* | 98.0 | 87.7 |
| | Std | 7.1 | 6.0 | 17.1 | 41.0 |
| | n | 3 | 3 | 3 | 3 |

TABLE 4-continued

| | | Factor VIII (FVIII) (%) | | | |
|---|---|---|---|---|---|
| | | 1 ml/kg PFC | 1 ml/kg PFC Dexam | 2 ml/kg PFC | 2 ml/kg PFC Dexam |
| 30 Days | Mean | 63.0 | 82.0 | 89.3 | 78.3 |
| | Std | 6.0 | 19.1 | 2.5 | 25.0 |
| | n | 3 | 3 | 3 | 3 |

\*Denotes a significant difference from baseline (p ≦ 0.05)
_Denotes a significant difference within a PFC dose group with and without pretreatment (p ≦ 0.05)
†Denotes a significant difference from baseline (p ≦ 0.01)
@Denotes a significant difference within a PFC dose group with and without pretreatment (p ≦ 0.01)

TABLE 5

| | | Fibrinogen (mg/dl) | | | |
|---|---|---|---|---|---|
| | | 1 ml/kg PFC | 1 ml/kg PFC Dexam | 2 ml/kg PFC | 2 ml/kg PFC Dexam |
| Baseline | Mean | 207.8 | 218.7 | 187.5 | 190.0 |
| | Std | 33.5 | 23.6 | 19.8 | 13.0 |
| | n | 3 | 3 | 3 | 3 |
| 4 Hour | Mean | 175.3 | 200.0 | 159.3 | 193.3 |
| | Std | 21.9 | 27.8 | 37.6 | 17.6 |
| | n | 3 | 3 | 3 | 3 |
| 6 Hour | Mean | 170.3 | 187.7 | 113.0†@ | 200.0 |
| | Std | 4.0 | 55.1 | 51.1 | 18.0 |
| | n | 3 | 3 | 3 | 3 |
| 1 Day | Mean | 247.0 | 248.7 | 146.7@ | 260.0† |
| | Std | 86.2 | 59.0 | 39.5 | 17.3 |
| | n | 3 | 3 | 3 | 3 |
| 2 Day | Mean | 276.7\* | 238.3 | 187.7 | 253.3\* |
| | Std | 58.4 | 42.5 | 36.6 | 30.6 |
| | n | 3 | 3 | 3 | 3 |
| 4 Days | Mean | 201.7 | 210.0 | 210.0 | 230.0 |
| | Std | 16.1 | 27.8 | 34.6 | 43.6 |
| | n | 3 | 3 | 3 | 3 |
| 7 Days | Mean | 156.0 | 192.7 | 183.3 | 195.7 |
| | Std | 1.7 | 21.9 | 10.4 | 33.9 |
| | n | 3 | 3 | 3 | 3 |
| 14 Days | Mean | 148.5 | 173.3 | 163.3 | 190.7 |
| | Std | 17.6 | 22.5 | 19.3 | 20.6 |
| | n | 3 | 3 | 3 | 3 |
| 30 Days | Mean | 150.0 | 166.7 | 152.3 | 169.0 |
| | Std | 13.2 | 14.4 | 5.9 | 15.9 |
| | n | 3 | 3 | 3 | 3 |

\*Denotes a significant difference from baseline (p ≦ 0.05)
_Denotes a significant difference within a PFC dose group with and without pretreatment (p ≦ 0.05)
†Denotes a significant difference from baseline (p ≦ 0.01)
@Denotes a significant difference within a PFC dose group with and without pretreatment (p ≦ 0.01)

TABLE 6

| | | Platelet Count (#/mm3) | | | |
|---|---|---|---|---|---|
| | | 1 ml/kg PFC | 1 ml/kg PFC Dexam | 2 ml/kg PFC | 2 ml/kg PFC Dexam |
| Baseline | Mean | 293,667 | 384,667 | 256,667 | 245,000 |
| | Std | 73,059 | 87,719 | 21,808 | 10,851 |
| | n | 3 | 3 | 3 | 3 |
| 4 Hour | Mean | 350,000 | 375,000 | 249,333 | 282,667 |
| | Std | 110,000 | 72,111 | 31,770 | 51,433 |
| | n | 3 | 3 | 3 | 3 |
| 6 Hour | Mean | 347,333 | 374,000 | 228,667 | 273,000 |
| | Std | 137,147 | 82,018 | 31,134 | 61,579 |
| | n | 3 | 3 | 3 | 3 |
| 1 Day | Mean | 313,333 | 387,000 | 218,667@ | 370,667 |
| | Std | 119,316 | 77,660 | 15,503 | 170,694 |
| | n | 3 | 3 | 3 | 3 |
| 2 Day | Mean | 159,000 | 268,000 | 108,333† | 223,333 |
| | Std | 54,617 | 112,468 | 64,485 | 75,593 |
| | n | 3 | 3 | 3 | 3 |
| 4 Days | Mean | 71,667\*@ | 193,333 | 45,333† | 86,000† |
| | Std | 16,803 | 146,401 | 14,012 | 21,703 |
| | n | 3 | 3 | 3 | 3 |
| 7 Days | Mean | 132,667\* | 213,333\* | 87,000† | 65,000† |
| | Std | 32,578 | 72,058 | 23,302 | 17,346 |
| | n | 3 | 3 | 3 | 3 |
| 14 Days | Mean | 264,333 | 311,333 | 148,000\* | 136,000\* |
| | Std | 51,082 | 72,858 | 31,225 | 3,464 |
| | n | 3 | 3 | 3 | 3 |
| 30 Days | Mean | 337,667 | 283,333 | 203,000 | 242,333 |
| | Std | 56,518 | 72,009 | 98,240 | 77,526 |
| | n | 3 | 3 | 3 | 3 |

\*Denotes a significant difference from baseline (p ≦ 0.05)
_Denotes a significant difference within a PFC dose group with and without pretreatment (p ≦ 0.05)
†Denotes a significant difference from baseline (p ≦ 0.01)
@Denotes a significant difference within a PFC dose group with and without pretreatment (p ≦ 0.01)

TABLE 7

| | | Triglycerides (mg/dl) | |
|---|---|---|---|
| | | 2 ml/kg PFC | 2 ml/kg PFC Dexam |
| Baseline | Mean | 45.5 | 33.8 |
| | Std | 17.7 | 24.9 |
| | n | 3 | 3 |
| 4 Hour | Mean | 47.0 | 40.7 |
| | Std | 11.3 | 16.7 |
| | n | 3 | 3 |
| 6 Hour | Mean | 51.0 | 31.7 |
| | Std | 16.7 | 15.1 |
| | n | 3 | 3 |
| 1 Day | Mean | 107.7\* | 25.0 |
| | Std | 51.1 | 11.3 |
| | n | 3 | 3 |
| 2 Day | Mean | 132.7\* | 87.3\* |
| | Std | 26.5 | 15.0 |
| | n | 3 | 3 |
| 4 Days | Mean | 115.0\* | 89.3 |
| | Std | 22.6 | 23.9 |
| | n | 3 | 3 |
| 7 Days | Mean | 68.3 | 45.7 |
| | Std | 2.5 | 25.9 |
| | n | 3 | 3 |

TABLE 7-continued

|  |  | Triglycerides (mg/dl) | |
|---|---|---|---|
|  |  | 2 ml/kg PFC | 2 ml/kg PFC Dexam |
| 14 Days | Mean | 54.7 | 54.7 |
|  | Std | 18.9 | 19.5 |
|  | n | 3 | 3 |
| 30 Days | Mean | 40.3 | 40.0 |
|  | Std | 5.0 | 15.6 |
|  | n | 3 | 3 |

*Denotes a significant difference from baseline (p ≦ 0.05)
_An underscored value denotes a significant difference within a PFC dose group with and without pretreatment (p ≦ 0.05)
†Denotes a significant difference from baseline (p ≦ 0.01)
@Denotes a significant difference within a PFC dose group with and without pretreatment (p ≦ 0.01)

TABLE 8

|  |  | Total Bilirubin (mg/dl) | | Direct Bilirubin (mg/dl) | |
|---|---|---|---|---|---|
|  |  | 2 ml/kg PFC | 2 ml/kg PFC Dexam | 2 ml/kg PFC | 2 ml/kg PFC Dexam |
| Baseline | Mean | 0.2 | 0.2 | 0.2 | 0.2 |
|  | Std | 0.0 | 0.1 | 0.0 | 0.1 |
|  | n | 3 | 3 | 3 | 3 |
| 4 Hour | Mean | 0.6* | 0.4* | 0.5* | 0.2 |
|  | Std | 0.3 | 0.1 | 0.5 | 0.1 |
|  | n | 3 | 3 | 3 | 3 |
| 6 Hour | Mean | 0.4* | 0.4* | 0.3 | 0.1 |
|  | Std | 0.1 | 0.1 | 0.1 | 0.0 |
|  | n | 3 | 3 | 3 | 3 |
| 1 Day | Mean | 0.4* | 0.2 | 0.4 | 0.1 |
|  | Std | 0.2 | 0.0 | 0.4 | 0.0 |
|  | n | 3 | 3 | 3 | 3 |
| 2 Day | Mean | 0.3 | 0.2 | 0.3 | 0.1 |
|  | Std | 0.2 | 0.1 | 0.2 | 0.0 |
|  | n | 3 | 3 | 3 | 3 |
| 4 Days | Mean | 0.2 | 0.2 | 0.2 | 0.2 |
|  | Std | 0.1 | 0.1 | 0.1 | 0.1 |
|  | n | 3 | 3 | 3 | 3 |
| 7 Days | Mean | 0.3 | 0.1 | 0.1 | 0.1 |
|  | Std | 0.1 | 0.1 | 0.0 | 0.0 |
|  | n | 3 | 3 | 3 | 3 |
| 14 Days | Mean | 0.3 | 0.2 | 0.1 | 0.1 |
|  | Std | 0.1 | 0.1 | 0.0 | 0.1 |
|  | n | 3 | 3 | 3 | 3 |
| 30 Days | Mean | 0.2 | 0.1 | 0.1 | 0.1 |
|  | Std | 0.1 | 0.1 | 0.0 | 0.0 |
|  | n | 3 | 3 | 3 | 3 |

*Denotes a significant difference from baseline (p ≦ 0.05)
_An underscored value denotes a significant difference within a PFC dose group with and without pretreatment (p ≦ 0.05)
†Denotes a significant difference from baseline (p ≦ 0.01)
@Denotes a significant difference within a PFC dose group with and without pretreatment (p ≦ 0.01)

TABLE 9

|  |  | SGOT-AST (U/L) | | LDH (U/L) | |
|---|---|---|---|---|---|
|  |  | 2 ml/kg PFC | 2 ml/kg PFC Dexam | 2 ml/kg PFC | 2 ml/kg PFC Dexam |
| Baseline | Mean | 32.8 | 27.8 | 165.2 | 124.8 |
|  | Std | 12.5 | 1.8 | 17.9 | 58.5 |
|  | n | 3 | 3 | 3 | 3 |
| 4 Hour | Mean | 143.3 | 89.3 | 743.3 | 311.0 |
|  | Std | 28.9 | 51.7 | 167.3 | 127.2 |
|  | n | 3 | 3 | 3 | 3 |
| 6 Hour | Mean | 270.7† | 127.0 | 1289† | 492.0 |
|  | Std | 53.0 | 54.0 | 448.7 | 119.7 |
|  | n | 3 | 3 | 3 | 3 |
| 1 Day | Mean | 549.0† | 166.7* | 3791.3† | 520.0 |
|  | Std | 240.2 | 61.8 | 1604.2 | 126.1 |
|  | n | 3 | 3 | 3 | 3 |
| 2 Day | Mean | 304.0† | 172.3* | 1588.3† | 558.7 |
|  | Std | 150.7 | 56.3 | 1155.5 | 303.0 |
|  | n | 3 | 3 | 3 | 3 |
| 4 Days | Mean | 73.7 | 81.3 | 451.7 | 299.0 |
|  | Std | 29.7 | 31.5 | 112.6 | 118.9 |
|  | n | 3 | 3 | 3 | 3 |
| 7 Days | Mean | 33.0 | 40.0 | 313.7 | 213.7 |
|  | Std | 7.0 | 8.5 | 60.7 | 62.7 |
|  | n | 3 | 3 | 3 | 3 |
| 14 Days | Mean | 22.3 | 25.3 | 228.0 | 164.3 |
|  | Std | 1.2 | 5.7 | 85.5 | 64.8 |
|  | n | 3 | 3 | 3 | 3 |
| 30 Days | Mean | 22.7 | 21.7 | 163.7 | 122.0 |
|  | Std | 0.6 | 2.1 | 36.2 | 3.2 |
|  | n | 3 | 3 | 3 | 3 |

*Denotes a significant difference from baseline (p ≦ 0.05)
_An underscored value denotes a significant difference within a PFC dose group without and without pretreatment (p ≦ 0.05)
†Denotes a significant difference from baseline (p ≦ 0.01)
@Denotes a significant difference within a PFC dose group with and without pretreatment (p ≦ 0.01)

The embodiments presented in the detailed description are provided by way of illustration only, and are not intended to limit the scope of the invention. Rather, this invention is defined by the appended claims and any equivalents thereto.

What is claimed is:

1. A method of improving the adverse effects of a perfluorochemical emulsion on the hemostatic system of a primate, comprising the steps of:
   intravenously administering a corticosteroid to a primate prior to intravenous administration of a perfluorochemical emulsion including a perfluorochemical, said corticosteroid administered at a dose of from about 0.2 mg/kg of body weight to about 6 mg/kg of body weight to improve the adverse effects of said perfluorochemical which occur at least about one day or more post administration of said perfluorochemical upon the hemostatic system of said primate; and
   subsequently intravenously administering said perfluorochemical emulsion.

2. The method of claim 1 wherein said corticosteroid is administered at a dose of about 1 mg/kg.

3. The method of claim 1 wherein said perfluorochemical is administered at a dose of from about 0.5 to about 10 ml/kg of body weight of said primate.

4. The method of claim 1 wherein said corticosteroid is dexamethasone.

5. The method of claim 1 wherein said perfluorochemical is selected from the group consisting of perfluorodichlorooctane, perfluorodecalin, perfluoromethyldecalin, perfluorodimethyldecalin, perfluorodimethyladamantane, perfluorooctylbromide, perfluoro-4-methyl-octahydroquinolidizine, perfluoro-N-methyldecahydroquinoline, F-methyl-1-oxa-decalin, perfluorobicyclo(5.3.0)decane, perfluorooctahydroquinolidizine, perfluoro-5,6-dihydro-5-decene, and perfluoro-4,5-dihydro-4-octene, chlorinated perfluorocarbons, and mixtures thereof.

6. The method of claim 5 wherein said perfluorochemical is perfluorodichlorooctane.

7. The method of claim 1 wherein said perfluorochemical emulsion contains said perfluorochemical in an amount of from about 15 v/v % to about 70 v/v %.

8. The method of claim 7 wherein said perfluorochemical emulsion contains said perfluorochemical in an amount of about 40 v/v %.

9. The method of claim 1 wherein said step of administering said perfluorochemical emulsion is begun within about several hours after said step of administering said corticosteroid.

10. The method of claim 9 wherein said step of administering said perfluorochemical emulsion is begun immediately following said step of administering said corticosteroid.

* * * * *